US011408895B1

(12) United States Patent
Chan et al.

(10) Patent No.: US 11,408,895 B1
(45) Date of Patent: Aug. 9, 2022

(54) ALLERGEN CHARACTERIZATION, POTENT ALLERGEN PRODUCT FORMULATION, COMPREHENSIVE ALLERGEN REAGENT, AND ALLERGY ASSAY

(71) Applicant: HOB Biotech Group Corp., Ltd., Suzhou (CN)

(72) Inventors: Sam Wei Polly Chan, Irvine, CA (US); Elaine Taine, Anaheim, CA (US); Scott Vande Wetering, Long Beach, CA (US); John Li, Suzhou (CN); Charles Lee, Suzhou (CN); Lin Qian, Suzhou (CN)

(*) Notice: Subject to any disclaimer, the term of this patent is extended or adjusted under 35 U.S.C. 154(b) by 376 days.

(21) Appl. No.: 16/379,754

(22) Filed: Apr. 9, 2019

Related U.S. Application Data

(60) Provisional application No. 62/831,230, filed on Apr. 9, 2019, provisional application No. 62/654,694, filed on Apr. 9, 2018.

(51) Int. Cl.
*G01N 33/68* (2006.01)
*G16B 15/00* (2019.01)
*G01N 27/447* (2006.01)
*G01N 33/02* (2006.01)

(52) U.S. Cl.
CPC ....... *G01N 33/68* (2013.01); *G01N 27/44743* (2013.01); *G01N 27/44791* (2013.01); *G01N 33/6854* (2013.01); *G16B 15/00* (2019.02); *G01N 33/025* (2013.01)

(58) Field of Classification Search
None
See application file for complete search history.

(56) References Cited

U.S. PATENT DOCUMENTS

| | | | |
|---|---|---|---|
| 4,226,853 A | 10/1980 | Marsh | |
| 4,605,557 A | 8/1986 | Stevens et al. | |
| 5,558,869 A | 9/1996 | Burks, Jr. et al. | |
| 5,731,157 A | 3/1998 | Miller et al. | |
| 5,770,698 A | 6/1998 | Berrens | |
| 6,449,562 B1* | 9/2002 | Chandler | G01N 33/537 702/19 |
| 7,576,184 B2 | 8/2009 | Cardosa et al. | |
| 8,044,345 B2 | 10/2011 | Lehmann et al. | |
| 8,361,460 B2 | 1/2013 | Morimatsu et al. | |
| 8,859,210 B2 | 10/2014 | Valenta et al. | |
| 8,871,688 B2 | 10/2014 | Brun et al. | |
| 9,170,231 B2 | 10/2015 | Young et al. | |
| 2005/0101031 A1 | 5/2005 | Hiller et al. | |
| 2006/0210590 A1* | 9/2006 | Hernandez | C07K 16/16 435/7.1 |
| 2010/0226933 A1 | 9/2010 | Thalhamer et al. | |
| 2011/0200641 A1 | 8/2011 | Hernandez et al. | |
| 2014/0206027 A1 | 7/2014 | Seppälä | |
| 2017/0112919 A1 | 4/2017 | Nadeau | |
| 2017/0219600 A1 | 8/2017 | Alving et al. | |

FOREIGN PATENT DOCUMENTS

| | | |
|---|---|---|
| EP | 0 026 007 | 4/1981 |
| EP | 2924047 | 9/2015 |
| WO | 1989010138 | 2/1989 |
| WO | 2007/031080 | 3/2007 |
| WO | 2011098569 | 8/2011 |
| WO | 2011151449 | 8/2011 |
| WO | 2013033713 | 3/2013 |

OTHER PUBLICATIONS

Besler et al., Immunological Characterization of Egg White Allergens Collected by Capillary Electrophoresis, Food and Agricultural Immunology, 10, (1998), p. 157-160. (Year: 1998).*

Nelson et al. "Allergen Immunotherapy Extract Preparation Manual" AAAAI Practice Management Resource Guide, 2014 edition. Jul. 19, 2014.

"Allergen immunotherapy: therapeutic vaccines for allergic diseases" WHO Position Paper, Geneva: Jan. 27-29, 1997.

Jones et al. "Allergy methods and protocols" (Abstract) Humana Press, 2008.

"Abstracts from the European Academy of Allergy and Clinical Immunology Congress Jun. 11-15, 2016 Vienna, Austria" Allergy European Journal of Allergy and Clinical Immunology vol. 71 • Supplement 102 • Aug. 2016.

Letter to Jubilant HollisterStier, LLC from Mary A. Malarkey, Director Office of Compliance and Biologies Quality Center for Biologies Evaluation and Research (Sep. 25, 2015).

Winter et al. "Immunoglobulin E Importance in Parasitic Infections and Hypersensitivity Responses" SArch Pathol Lab Med—vol. 124, Sep. 2000, pp. 1382-1385.

(Continued)

*Primary Examiner* — Ellen J Marcsisin
(74) *Attorney, Agent, or Firm* — The Law Office of Austin Bonderer, PC; Austin Bonderer

(57) ABSTRACT

A method for detecting and quantifying allergen components of a substance is described herein. A method can include obtaining an Ig sample derived from two or more individuals, and one or more capillaries comprising allergenic biologics adhered thereto. The Ig sample can be applied to the one or more capillaries and allergen component and molecules that has bound with the Ig sample, can be detected in the one or more capillaries. A molecular weight and/or frequency of appearance, an isoelectric charge and/or frequency of appearance, a molecular functional group and/or frequency of appearance or a combination thereof, of the allergen component can be recorded. Furthermore, methods for determining the minimum and maximum concentrations of the detected allergen components for pre-determined platforms, formulating an allergen product using the determined concentration ranges and applying the allergen product to result an effective assay are described.

8 Claims, 9 Drawing Sheets

(56) References Cited

OTHER PUBLICATIONS

Spiric et al. "Mass spectrometry to complement standardization of house dust mite and other complex allergenic extracts" Clinical & Experimental Allergy, 47, 604-617, 2017.
AAAAI Committee on Allergen Standardization "AAAAI Position Statement: The Use of Standardized Allergen Extracts" May 1997.
Takai et al. "Japanese Society of Allergology task force report on standardization of house dust mite allergen vaccines—Secondary publication" Allergology International 64 (2015), pp. 181-186.
AAS "What Makes an Allergen an Allergen" Allergy, Mar. 1978.
Esch "Manufacturing and standardizing fungal allergen products" Nov. 2003.
Boschetti et al. "The Discover of Low-Abundance Allergens by Proteomics Analysis Involving Combinatorial Peptide Ligand Libraries", Jacobs Journal of Allergy and Immunology, http://allergyandimmunology.jacobspublishers.com/index.php/j-j-aller-immuno-2-2-015, Mar. 11, 2015.
Ferranti et al. "Proteomic and immunochemical characterization of food allergens of plant origin: The hazelnut (*Corylus avellana*) case of study", Dottorato di ricerca in Scienze e Tecnologie delle Produzioni Agro-Alimentari XXV ciclo, http://www.fedoa.unina.it/9331/1/Nitride_Chiara_25.pdf, 2013.
Hofer et al. "Tree pollen allergens—an update from a molecular perspective" European Journal of Allergy and Clinical Immunology, Aug. 6, 2015.

* cited by examiner

ALLERGEN CHARACTERIZATION, POTENT ALLERGEN PRODUCT FORMULATION, COMPREHENSIVE ALLERGEN REAGENT, AND ALLERGY ASSAY

FIELD

The subject matter herein generally relates to technology in the field of immunology and allergology. In particular, the invention relates to a process for detecting and quantifying allergen components and composition of an allergen source.

BACKGROUND

In most allergic hypersensitivity reactions, the immune system produces immunoglobulin (Ig) type E (IgE), which is the least abundant isotype of immunoglobulin antibodies in blood and is expressed in relatively small amount (Johansson, S. The Discovery of IgE, J Allergy Clin Immunol. 2016; 137 (6): 1671-1673). Specific IgE (sIgE) concentration can be detected with in vitro assays that have been available for decades using allergen extracts. However, products from different suppliers produce inconsistent results due to the lack of standardization or a stringent standardization requirement. Commercially available allergen products for in vivo application such as allergen extracts for skin prick tests and immunotherapy are either standardized or non-standardized. Some common standardized products are cat hair and pelt, mite, grass pollens, short ragweed, and venom (https://www.fda.gov/BiologicsBloodVaccines/Allergenics/ucm391514.htm), Allergens are standardized by comparing to U.S. reference standard for potency maintained and distributed by US Food and Drug Administration (FDA), the Center for Biologics Evaluation and Research (CBER) (AAAAI, Use of standardized allergen extracts; 1997; https://www.fda.gov/BiologicsBloodVaccines/Allergenics/ucm391514.htm). Most standardized allergens are required to include defined major components and list their overall potency, expressed in bioequivalent allergy unit/mL, a form of measurement of how much allergic reaction is anticipated from a group of highly sensitive allergic subjects in response to a skin test using the allergen product, coupled with the evaluation obtained by immunochemical techniques to the major components (WHO Position Paper, Allergen immunotherapy: therapeutic vaccines for allergic diseases; 1997). Non-standardized products with no U.S. reference standards contain allergen extracts with undefined composition of proteins and other biologics from the allergen source, which may vary greatly due to the source of allergen and extraction method used.

An allergen component is regarded as a major component, generally, if more than 50% of sensitized individuals express IgE in response to it, while other allergen components are largely regarded as minor components (less than 50% of sensitized individuals express IgE in response). Each sIgE is highly specific and binds to unique IgE-binding epitopes of allergen components (Bufe, Significance of IgE-binding epitopes in allergic disease, Allergy Clin Immunol 2001; 107:219-21), and each component could have various IgE-binding epitopes (www.iebd.org). Most allergen sources have more than one allergen component (Matricardi, Kleine-Tebbe et al., EAACI Molecular Allergology User's Guide, Pediatr Allergy Immunol. 2016 May; 27 Suppl 23:1-250), of which, typically, some are major and some are minor components. Sensitized individuals may have multiple different allergen component-specific IgEs corresponding to various components in a single allergen source. For example, a person can be allergic to one or more components of peanut (and sometimes not all those components are present in all peanut or peanut extracts). Thus, they may present a response to the major, minor, or both major and minor components. Once expression of IgE is initiated in response to the presence of an allergen component, whether a minor or a major component, complex allergic inflammatory tissue reactions may follow (Aas, What Makes an Allergen an Allergen, Allergy. 1978, 33:3-14). Adverse actions of IgE can be categorized by type I hypersensitivity with anaphylaxis, rhinitis, and asthma as some of the clinical examples (Winter, Hardt, et al., Immunoglobulin importance in parasitic infections and hypersensitivity responses, Arch Pathol Lab Med. 2000 September; 124(9):1382-5).

The inventors in the US PreGrant Pub. US20110200641A1 have detected numerous patients exhibiting strong IgE response toward minor components. The study and regulation of minor components is held back due to difficulties in identification, IgE sample availability, and protein sourcing limitations, even though a reaction to such a minor component can be as severe or even life-threatening as any major component.

Allergen materials that are used to detect specific IgE in common diagnostic assays are crude extracts from native allergen sources with or without supplementation with recombinant major allergen component proteins known to be unstable or in low concentration. A fairly comprehensive list of current allergy assays relying on native allergenic source available is listed in US PreGrant Pub. US20050101031A1. Native allergen sources are mainly defined by. Genus species without other important specifics such as the stage of growth or defined body parts or fluid of the species (Esch, R. Manufacturing and standardizing fungal allergen products, J. Allergy Clin Immunol. 2003 November; 113 (2): 200-45). The lack of specifics leads to huge composition discrepancy even among batches of allergen extract from the same supplier and subsequently affecting the reproducibility of the allergy diagnostics assay and the effectiveness of immunotherapy.

The standardization program mentioned earlier focuses on major allergen components that are highly studied. The crystal structure of the major components may have been discovered, and the protein produced recombinantly so that a large quantity of the components can be used for protein characterization, binding kinetics study or supplementing allergen materials for optimized allergy tests. However, there are still many unidentified and uncharacterized allergen components, and the prevalence of sensitization to these components is considered too low by the regulatory agencies and advocates to justify assigning limited resources to advance their study. AAAAI, a professional society whose mission is advancement of the knowledge of allergies, asthma and immunology for optimal patient care, stated that "there are several hundred extracts currently being marketed, and it is neither feasible nor economical to standardize them all. There will remain some extracts that are commercially available but have not been characterized or assessed for allergen content. This is usually because these allergens affect only a small number of patients with allergy or because the allergens occur in limited geographic area." (emphasis added) Even as new technologies have become available to define allergen content in mass units, AAAAI stated the application of these new technologies to measure specific allergens "should focus on proteins of well-established allergenic importance, which fulfill criteria for inclusion in the WHO/IUIS nomenclature (e.g., Fel d 1, Der p 1 and Lol p 1)" (AAAAI Position Statement: The Use of Standardized Allergen Extracts, 1997 May emphasis added).

The position put forth in 1997 by AAAAI towards allergen characterization remains similar due to their focus on serving the majority of allergy patients and value placed on how to apply resources. The quantity of each minor allergen component in many single allergens is, therefore, a result of the natural abundance. Break-through technology is needed to handle the complexity of each allergen, the vast list of allergens with uncharacterized components, and to develop comprehensive and balanced allergy diagnostic tests and therapeutic solutions for patients sensitized to minor allergen components. Hernandez et al. proposed to adjust the quantities of major and minor allergen components in immunogenic compositions using therapeutic administration limits in the light of improving the safety of allergen vaccines in US PreGrant Pub. US20110200641A1. However, for in vitro application, the detection limit is directly related to biologics concentrations and assay parameters. Antigen-antibody binding kinetic, represented in equation (1) is affected by a number of factors, including temperature, pH, ionic strength of buffers, concentrations of antigen and antibody and the duration of incubation provided by the allergenic assay (Factors affecting the antigen-antibody reaction, Blood Transfus. 2007 November; 5(4): 227-240).

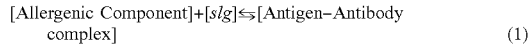

$$[\text{Allergenic Component}] + [sIg] \leftrightarrows [\text{Antigen-Antibody complex}] \qquad (1)$$

Therefore, the minimum amount of an allergen component that can detect a sIgE concentration at the clinically significant level is assay and reaction platform dependent. Sample applicable immunoassay platform is an in vitro diagnostic (IVD) device.

To assess the component coverage of allergen extracts, it is hereby suggested profiling all allergen extracts by their total protein and/or biologics composition quantitatively, along with their responses in an immunoassay with Ig samples (e.g., relevant patient serum or plasma samples). The resulting profile could be a marked improvement on the existing standardization program used to release in vitro diagnostic assays and allergen extracts for in vivo diagnostics into the market.

Allergen components in crude extracts were initially identified qualitatively by SDS-PAGE followed by Western Blot using human plasma or serum samples which aimed to provide the molecular weight of the components and confirm their role as an antigen. However, the SDS-PAGE followed by Western Blot fails to provide an accurate quantitative abundance measurement of each component in the extract. Moreover, because of the low sIgE concentration in IgE samples, conventional Western Blot requires 200 μL or more of IgE sample for each procedure, which amounts to an impractical volume for any meaningful study that asks for single to double-digit milliliters of each IgE sample. Therefore, the present inventors are devoted to developing a feasible process and platform that uses twenty to forty times less IgE sample volume, to adequately profile allergen extracts and biologics, that could benefit a broader range of allergy patients, including those who are sensitized to minor and uncharacterized allergen components, with minimized effort.

BRIEF DESCRIPTION OF THE DRAWINGS

Implementations of the present technology will now be described, by way of example only, with reference to the attached figures, wherein.

SUMMARY OF SOME OF THE EMBODIMENTS

Figure 1:
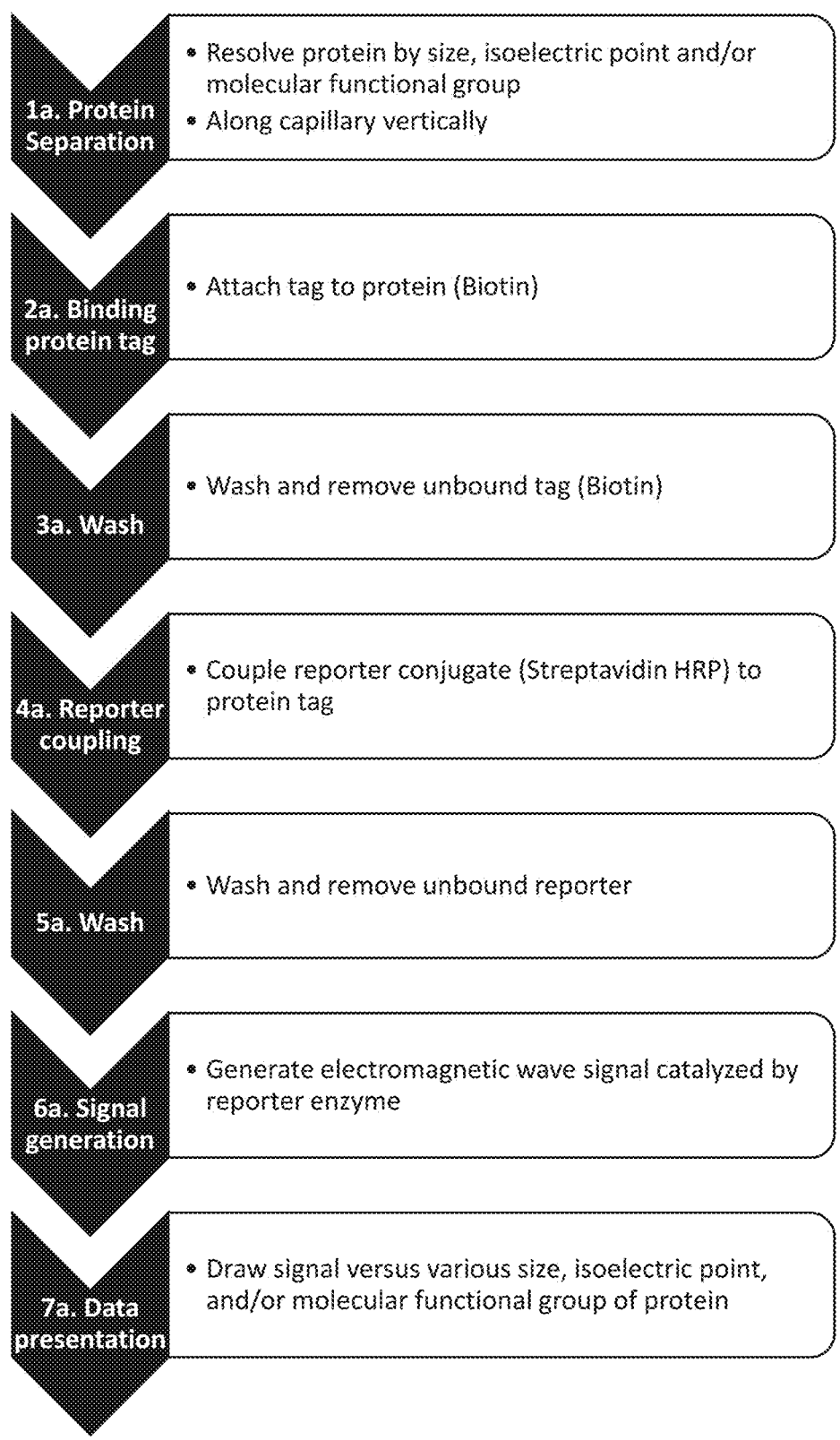
FIG. 1 shows an embodiment of a protein content characterization process.

The disclosure presented herein discloses, but is not limited to; the methods and systems for allergen characterization; biologics characterization, allergy assay formulation, reagent formulation for allergen products and/or allergy assays.

One embodiment of a method comprises an allergen characterization method. The allergen characterization comprises: applying a biologics along one or more resolving material filled capillaries using capillary electrophoresis resulting in linearly separated biologics, wherein the biologics are linearly separated, during capillary electrophoresis, according to size, isoelectric charge and/or molecular functional group resulting in linearly separated biologics; blocking the empty capillary space with inert protein; supplying an immunoglobulin (Ig) sample to the one or more capillaries resulting in bound Ig, the sIg, and unbound Ig; washing away unbound Ig; tagging the bound Ig with a reporter; washing away unbound Anti-Ig; and generating an allergen component signal. It is understood that biologics can comprise of protein and other molecules that bind with their sig.

One embodiment of a method comprises allergen characterization and biologics content characterization. The allergen characterization comprises applying biologics along one or more resolving material filled capillaries using capillary electrophoresis resulting in linearly, separated biologics, wherein the biologics are linearly separated, during capillary electrophoresis, according to size, isoelectric charge, and/or molecular functional group resulting in linearly separated biologics; blocking the empty capillary space with inert protein; supplying an immunoglobulin GO sample to the one or more capillaries resulting in bound Ig and unbound Ig; washing away unbound Ig; tagging the bound Ig with a reporter; washing away unbound Anti-Ig; and generating an allergen component signal.

One embodiment of a method comprises allergen characterization. The allergen characterization comprises placing a reservoir plate containing biologics in a capillary electrophoresis device; applying the biologics along one or more resolving material filled capillaries, during capillary electrophoresis by the capillary electrophoresis machine, resulting in linearly separated biologics, wherein the biologics are linearly separated according to the individual biologic's size, isoelectric charge and/or molecular functional group resulting in linearly separated biologics; blocking the empty capillary space with inert protein; supplying an immunoglobulin (Ig) sample to the one or more capillaries resulting in bound Ig and unbound Ig; washing away unbound Ig; tagging bound Ig with a reporter, washing away unbound Anti-Ig; and generating an allergen component signal.

One embodiment of a method comprises an allergen reagent that can be used to assure the quality of allergy products to represent many, if not all, of the major and minor components present n an allergen. A selected number of allergen components are formulated, with a defined range of concentration, into the allergy assay, which is from a minimum concentration that results in a default threshold value [Limit of Detection (LOD)] to a maximum concentration that can still allow all other components to be loaded with minimum concentrations or higher. The minimum, and thus maximum, concentrations of each component are assay- and platform-dependent, and the concentrations for each assay and platform will be determined using those assays and platforms.

One embodiment of a method, that can be used to assure the quality of allergen products to represent many, if not all, of the major and minor components and/or other biologics present in an allergen, comprises placing an Ig solution at the limit of detection to titrate for the minimum concentration of identified components using monosensitized environment on a predetermined platform. After the minimum concentration of each selected components is defined, a theoretical maximum concentration of each component will be calculated based on total biologic binding capacity of the predetermined platform. The concentration of each component in an allergy extract will then be modified to the defined range by traditional biologics purification method such as chromatography, filtering with a membrane having a molecular weight cut off, or supplementing with pure components that can be obtained by purification or recombinant method. The allergy extract can then be assured to have a sufficient amount of each known and/or desired component to accurately test individuals" reactiveness to an allergen, major and minor components and other biologics.

One embodiment of a method comprises testing for sensitization using a comprehensive allergen product. An allergen solution, comprising the comprehensive allergen product formulated with selected components that are all within defined concentration range, is first applied along one or more resolving material filled capillaries using capillary electrophoresis. The result comprises linearly separated biologics, wherein the biologics are linearly separated, during the capillary electrophoresis, according to size, isoelectric charge and/or molecular functional group. Samples or Ig standard solutions, with known concentrations of sIgs, are supplied to these capillaries resulting in bound Ig, from the sIg, and unbound Ig. The bound Ig is tagged with a reporter, and an allergen component signal is then generated. Each patient sample signal is compared to Ig standard solutions, and their individual specific Ig concentration is quantified.

One embodiment of a method for testing one or more patients for sensitization to many if not all major and minor components, of an allergen comprises applying a comprehensive allergen product, or derivative thereof (e.g. solution of the comprehensive allergen product if the comprehensive allergen product is not in liquid form), to a resolving material filled capillary so that the components of the comprehensive allergen product are linearly separated (e.g., by biologics size, isoelectric charge, and/or molecular functional group). Samples, comprising from the one or more patients are supplied to the capillaries resulting in bound Ig and unbound Ig. The bound Ig is tagged with a reporter, and an allergen component signal is then generated.

It is to be understood that the summary presented herein is in no way meant to limit the scope of the invention.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated to illustrate details and features better. The description is not to be considered as limiting the scope of the embodiments described herein. It should be noted that references to "an" or "one" embodiment in this disclosure are not necessarily to the same embodiment, and such references mean at least one.

Several definitions that apply throughout this disclosure will now be presented.

The term "inside" indicates that at least a portion of a region is partially contained within a boundary formed by the object. The term "comprising" means "including, but not necessarily limited to"; it specifically indicates open-ended inclusion or membership in a so-described combination, group, series and the like. The term "Ig sample" means sample containing Immunoglobulin, either in native forms, chimeric forms, or resembled by artificial carriers containing the immunogenic sequence that binds with antigens. Samples "Ig sample" are human plasma, human serum, and monoclonal antibodies solution. The term "Ig solution at limit of detection" means a solution comprising one or more Igs, each corresponding to a specific antigen, in a concentration that enables a positive result approximately equal to the limit of detection of a predetermined platform when exposed to its corresponding antigen. The term component refers to any biologic capable of being bound by an Ig.

Further definitions include:

AAAAI—American Academy of Allergy, Asthma & Immunology.

BCA assay—a protein quantification assay utilizing Bicinchoninic Acid (BCA) as the reporting agent.

Biologics—protein, molecules or other substance that contains components of living organisms BSA—Bovine Serum Albumin, a common blocking reagent to reduce non-specific binding CLIA—Chemiluminescence Immunoassay, a technique used to detect and quantify the presence of an analyte, usually antibodies or antigens, through detecting the amount of chemiluminescence emitted by enzyme linked conjugates in the testing reagent.

Epitopes—A region of an antigen with a defined amino acid sequence recognized by the immune system.

FPLC—Fast Protein Liquid Chromatography, a technique used to purify biomolecules.

HRP— Horseradish Peroxidase, an enzyme commonly used to oxidize reporter substrate emit a detectable signal.

kDa—Kilo Dalton, a common unit used to describe the molecular mass of proteins

Molecules—composing unit of any chemical compound formed by a group of atoms bound together MWCO—Molecular Weight Cut-Off PBS— Phosphate Buffered Saline SDS-PAGE—Sodium Dodecyl Sulfate Polyacrylamide Gel Electrophoresis, a conventional technique used to separate and visualize protein WHO/IUIS—World Health Organization/International Union of Immunological Societies The present disclosure comprises a novel and systematic method to profile the molecular weight of monomeric allergen components of an allergen source along with the prevalence of sensitization to the profiled components in a population, including both major and minor components profiled.

Referring to FIG. 1, a flowchart is presented in accordance with an example embodiment of a method. The example method is provided by way of example, as there are a variety of ways to carry out the method. The method described below can be carried out using the schematic configurations illustrated in FIG. 3, for example, and various elements of these figures are referenced in explaining an exemplary method. Each block shown in FIG. 1 represents one or more processes, methods or subroutines, carried out in the example method. Furthermore, the illustrated order of blocks is illustrative only, and the order of the blocks can change according to the present disclosure. Additional blocks can be added, or fewer blocks may be utilized, without departing from this disclosure. The example method can begin at protein content protein separation 1a.

Figure 2:
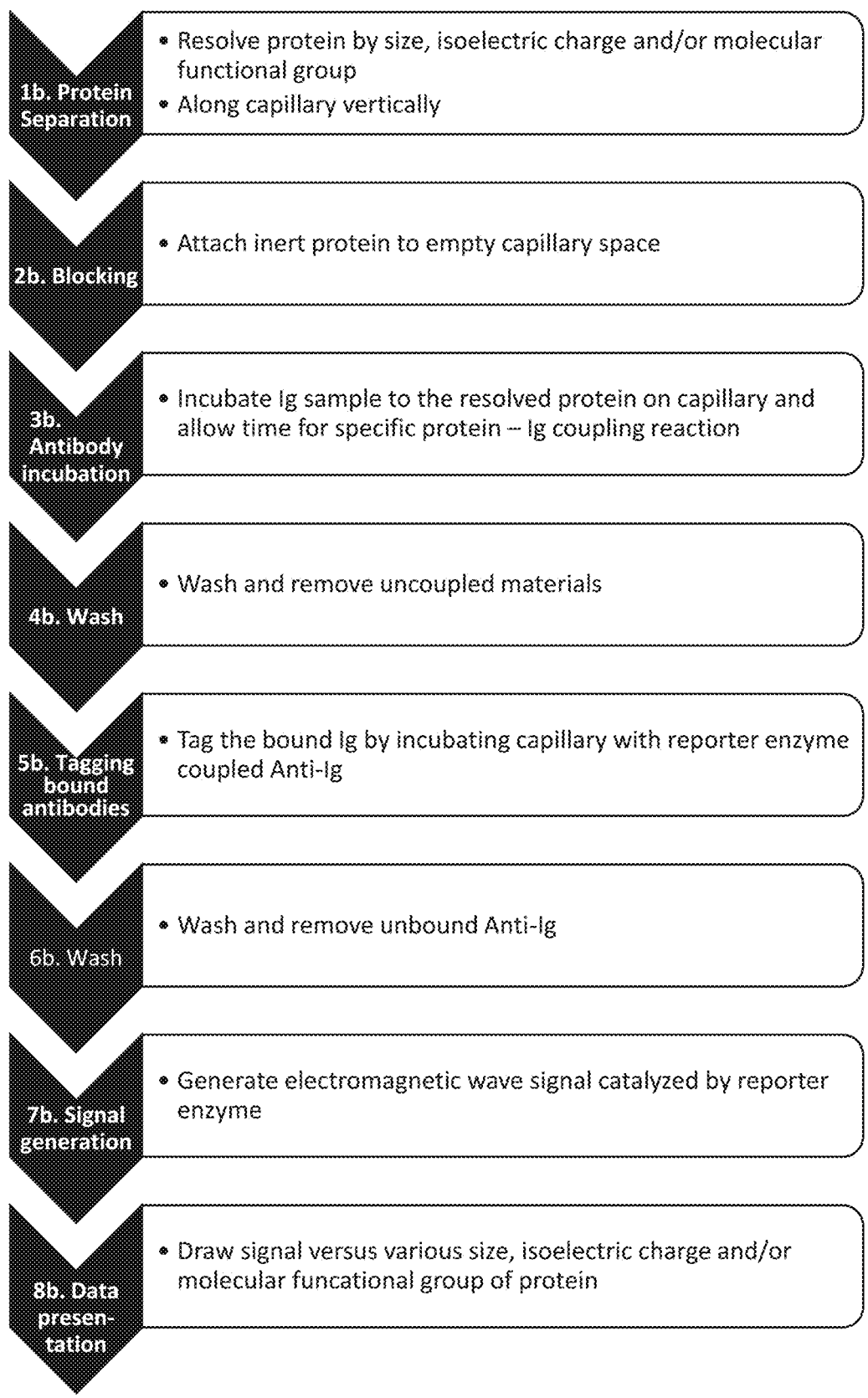
FIG. 2 shows an embodiment of an allergen characterization process.

In some embodiments, the protein content characterization method (an example of which is shown in FIG. 1) is performed before or contemporaneous with the allergen characterization method (an example of which is shown in FIG. 2).

At protein content protein separation 1a, during the protein content characterization method, the first process includes detecting the protein size, isoelectric charge and/or molecular functional group and abundance of the different proteins. During the protein content characterization, the first step is protein content protein separation 1a; wherein protein is applied to a capillary electrophoresis system where proteins of different sizes, isoelectric charges and/or molecular functional group are separated from others using electrophoresis in a linear orientation along the resolving material filled capillaries resulting in linearly separated proteins. It is to be understood that while most of this description is discussed in terms of linearly separated proteins, any other biologics that bind with Ig and that are able to be separated by any acceptable means can be used. The second step is binding protein tag 2a; wherein proteins within the capillary are bound with a tag that can be detected in the subsequent reactions. The third step is remove unbound tags 3a; this is a wash step wherein unbound tags are washed away from the capillaries. The fourth step, reporter coupling 4a; binds a reporter conjugate to the protein tag, resulting in a coupled reporter, that aims to generate a reportable signal. The fifth step, remove unbound reporter 5a; is a wash step wherein unbound reporter is washed away from the capillary. The sixth step is protein content signal generation 6a; wherein the reporter substrate is catalyzed and produces an electromagnetic wave resulting in an electromagnetic signal. The seventh step, protein content data presentation 7a; is a data presentation step wherein the magnitude of the electromagnetic wave is plotted against increasing size, isoelectric charge, and/or various molecular functional group of the protein. This can be done by a graphical representation, computer processing, and/or digital storage.

Figure 5:
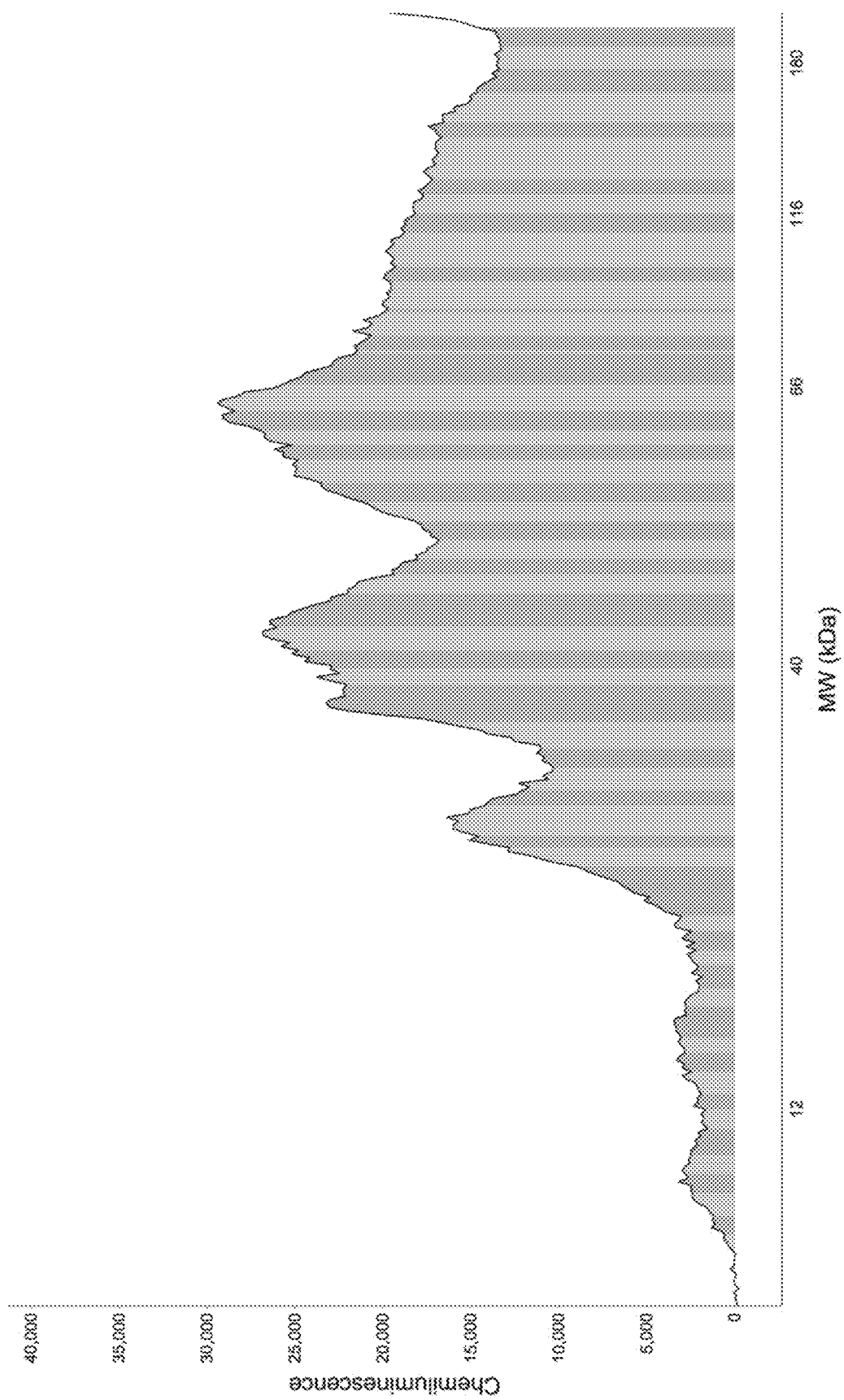
FIG. 5 shows a protein content chromatogram of a sample pistachio extract from a food supplier.
Figure 6:
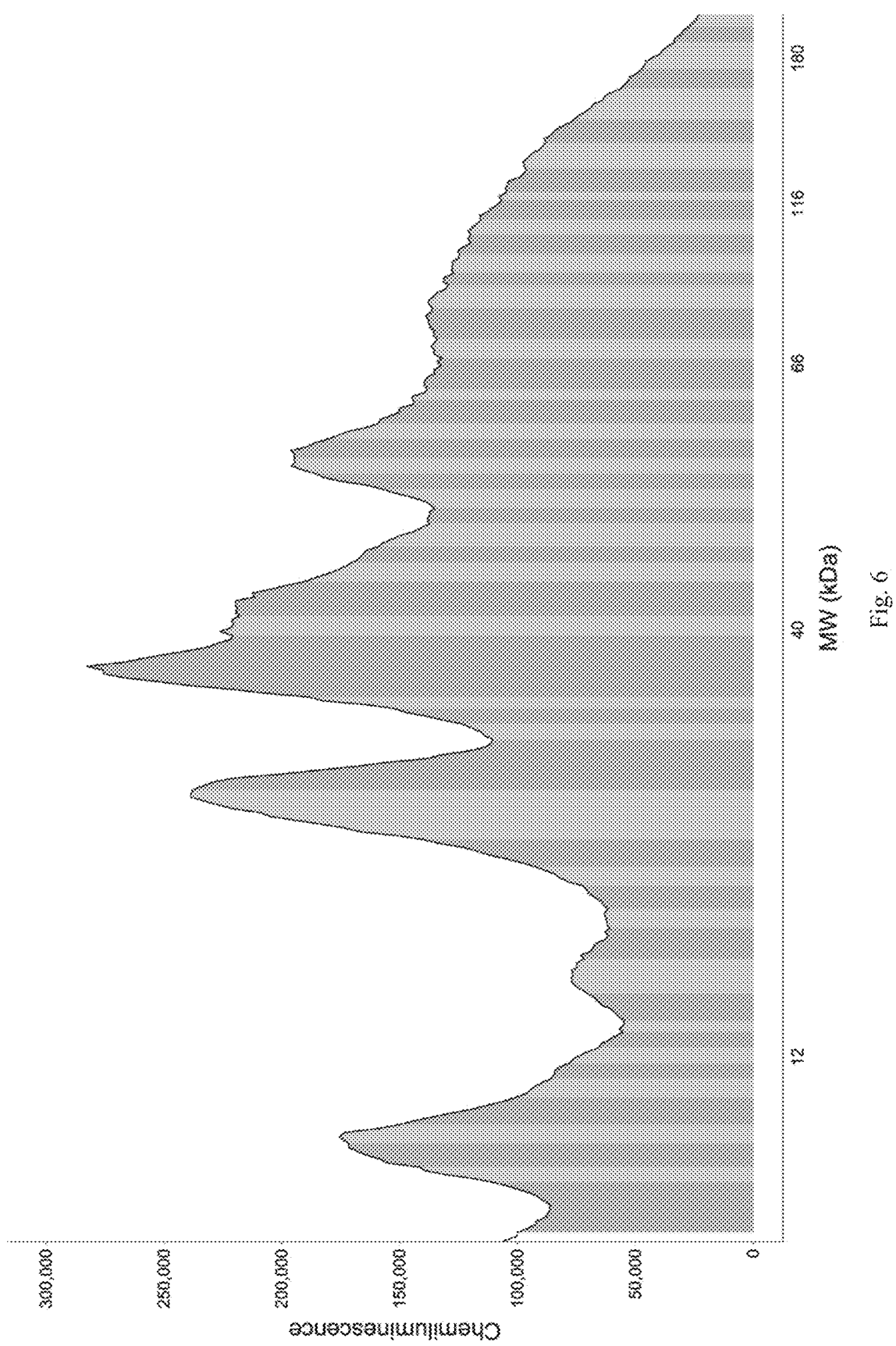
FIG. 6 shows a protein content chromatogram of a sample pistachio extract from an allergen material supplier.

A sample protein content chromatogram obtained by the example below is provided in FIGS. 5 and 6.

Figure 4:
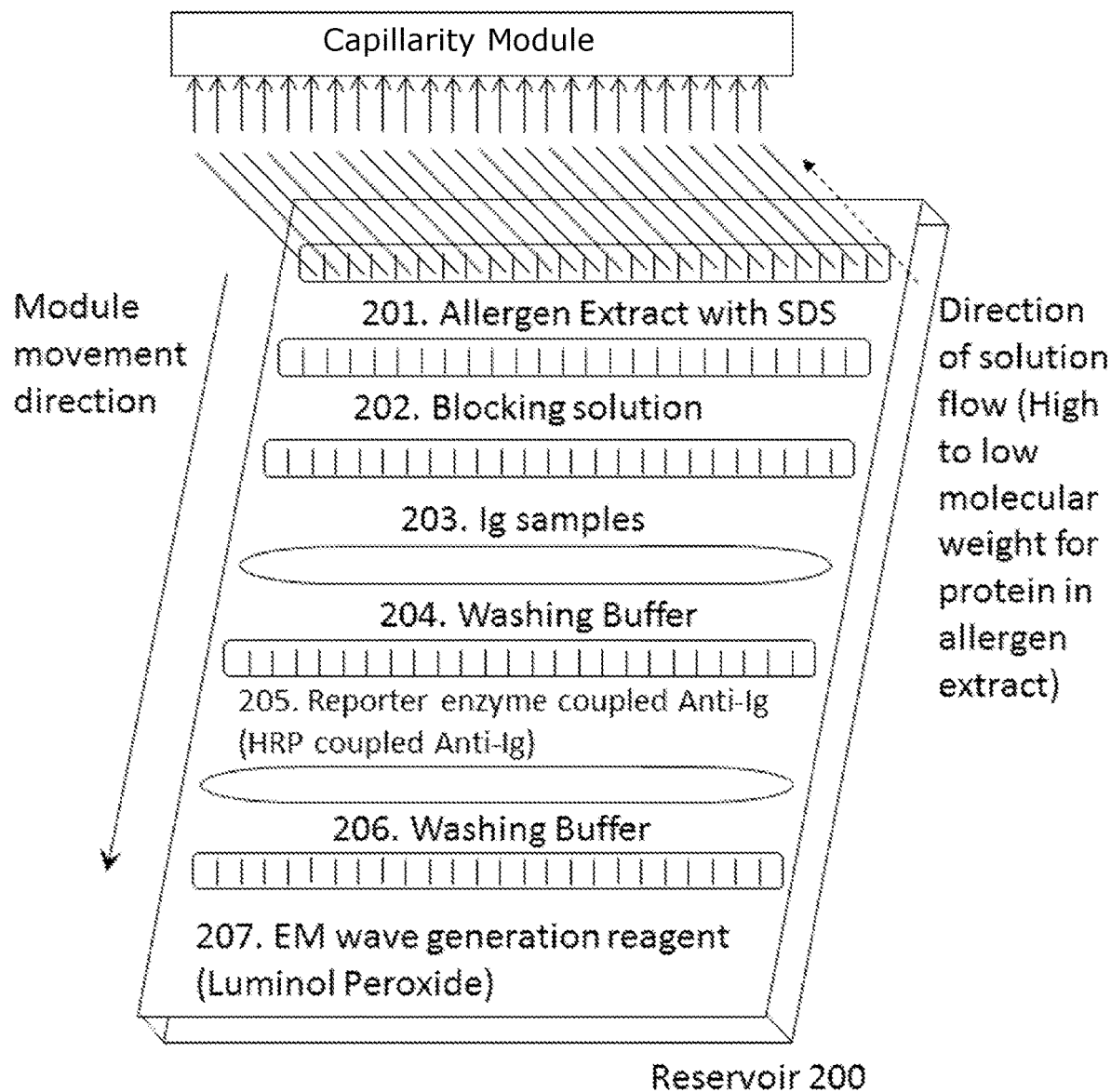
FIG. 4 shows an embodiment of the capillary electrophoresis set-up for an allergen characterization process.

Referring to FIG. 2, like above, a flowchart is presented in accordance with an example embodiment of a method. The example method is provided by way of example, as there are a variety of ways to carry out the method. The method described below can be carried out using the schematic configuration illustrated in FIG. 4, for example, and various elements of these figures are referenced in explaining an exemplary method. Each block shown in FIG. 2 represents one or more processes, methods or subroutines, carried out in the example method. Furthermore, the illustrated order of blocks is illustrative only, and the order of the blocks can change according to the present disclosure. Additional blocks can be added, or fewer blocks may be utilized, without departing from this disclosure. The example method can begin at protein separation 1b.

Protein separation 1b, during the detection of allergen components process, comprises applying the same allergenic extract protein solution to the same capillary electrophoresis system as during the protein content characterization (but with a different module of capillaries or different capillaries with the same module) and proteins of different sizes, isoelectric charge and/or molecular functional group are separated from others during electrophoresis in a linear orientation. The blocking 2b is a blocking step; wherein the capillary is blocked and capillary space that is not occupied by protein, of the corresponding size, is coated with an inert protein that will not participate in any subsequent reactions. The third step, antibody incubation 3b, is an antibody incubation step wherein Ig sample (e.g., patient serum or monoclonal antibodies solution) is applied to the inside of the capillary and allowed time for a protein—Ig coupling. The fourth step, remove uncoupled materials 4b, is a wash step wherein uncoupled materials are washed and removed from the capillary. The fifth step, tagging bound antibodies 5b, is an antibody tagging step wherein a reporter enzyme coupled anti-Ig solution is supplied to the inside surface of the capillaries and any capillary bound Ig couple with the anti-Ig supplied aiming to generate a reportable signal. The remove unbound Anti-Ig 6b is a wash step wherein uncoupled materials are washed and removed from the capillary. The seventh step is signal generation 7b wherein the reporter substrate is catalyzed and produces an electromagnetic wave resulting in an electromagnetic signal. The eighth step, data presentation 8b, is a data presentation step, often in a graphical representation, wherein the magnitude of the electromagnetic wave is plotted against increasing size, isoelectric charge and/or molecular functional group of the protein.

Figure 7:
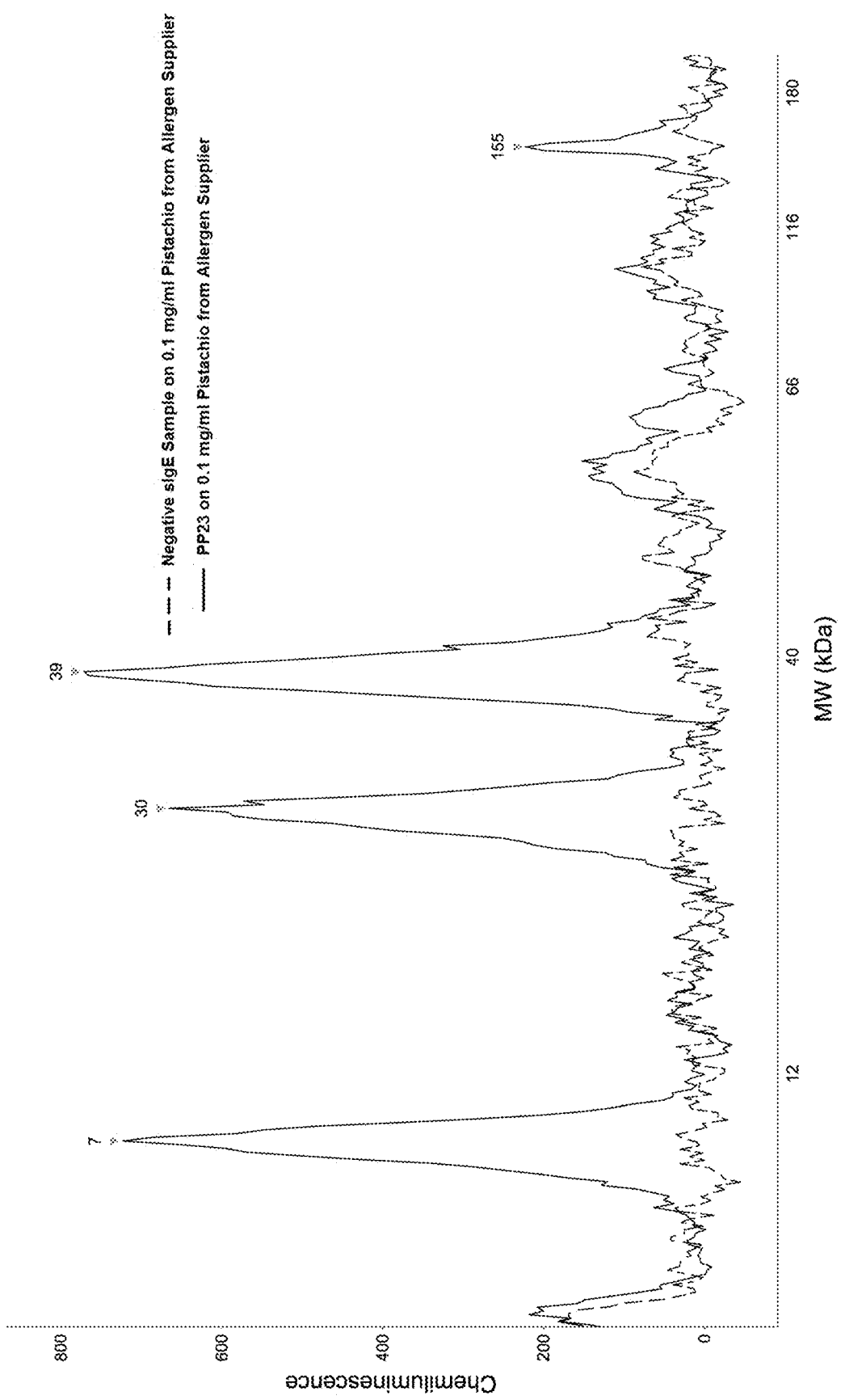
FIG. 7 shows a result of an example capillary electrophoresis immunoassay chromatogram of pistachio extract with an Ig sample and a negative control (Ig sample with low total IgE content)
Figure 8:
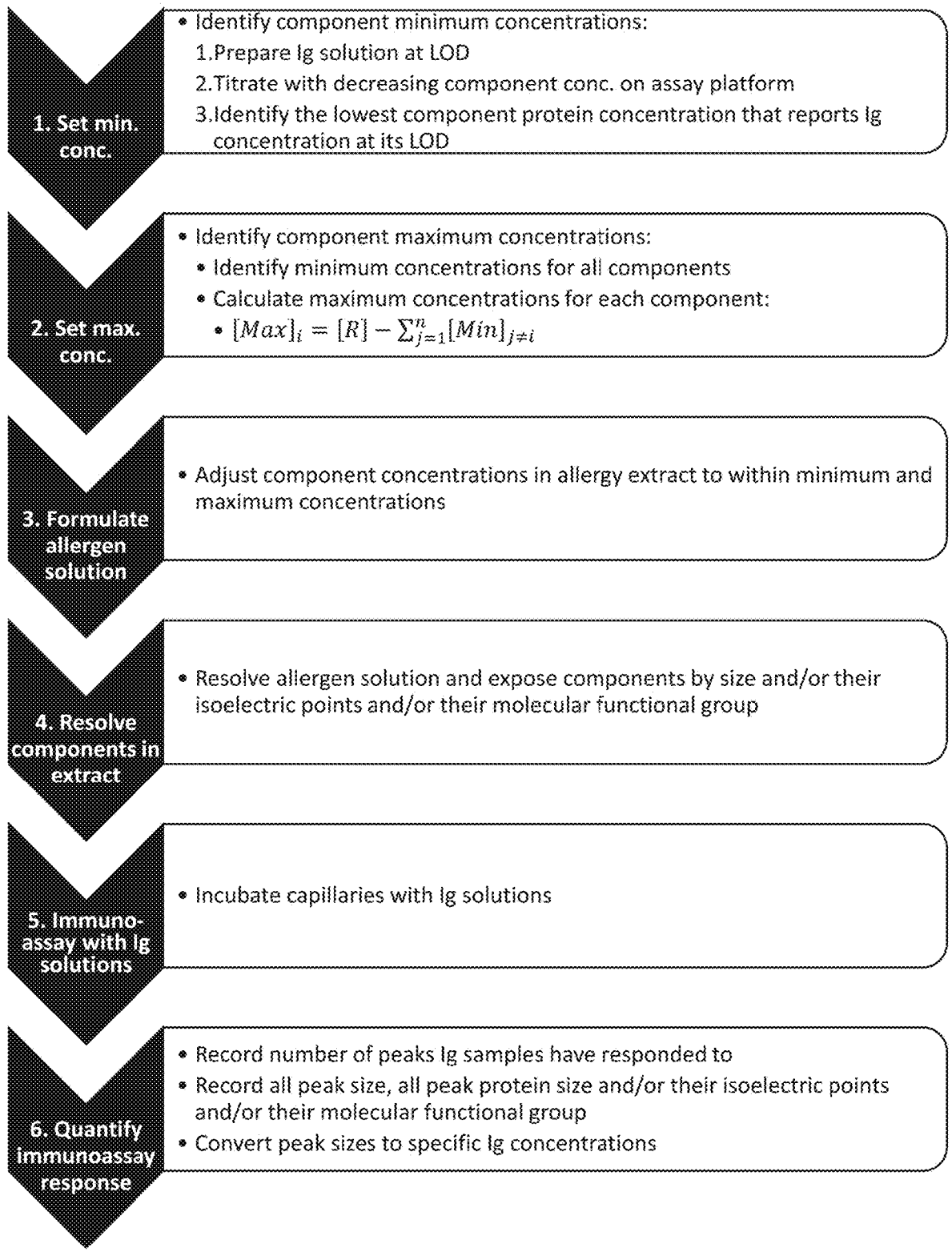
FIG. 8 shows an embodiment of an Ig quantitation process.

A sample allergen detection chromatogram, from the example below, can be seen in FIG. 7.

Figure 3:
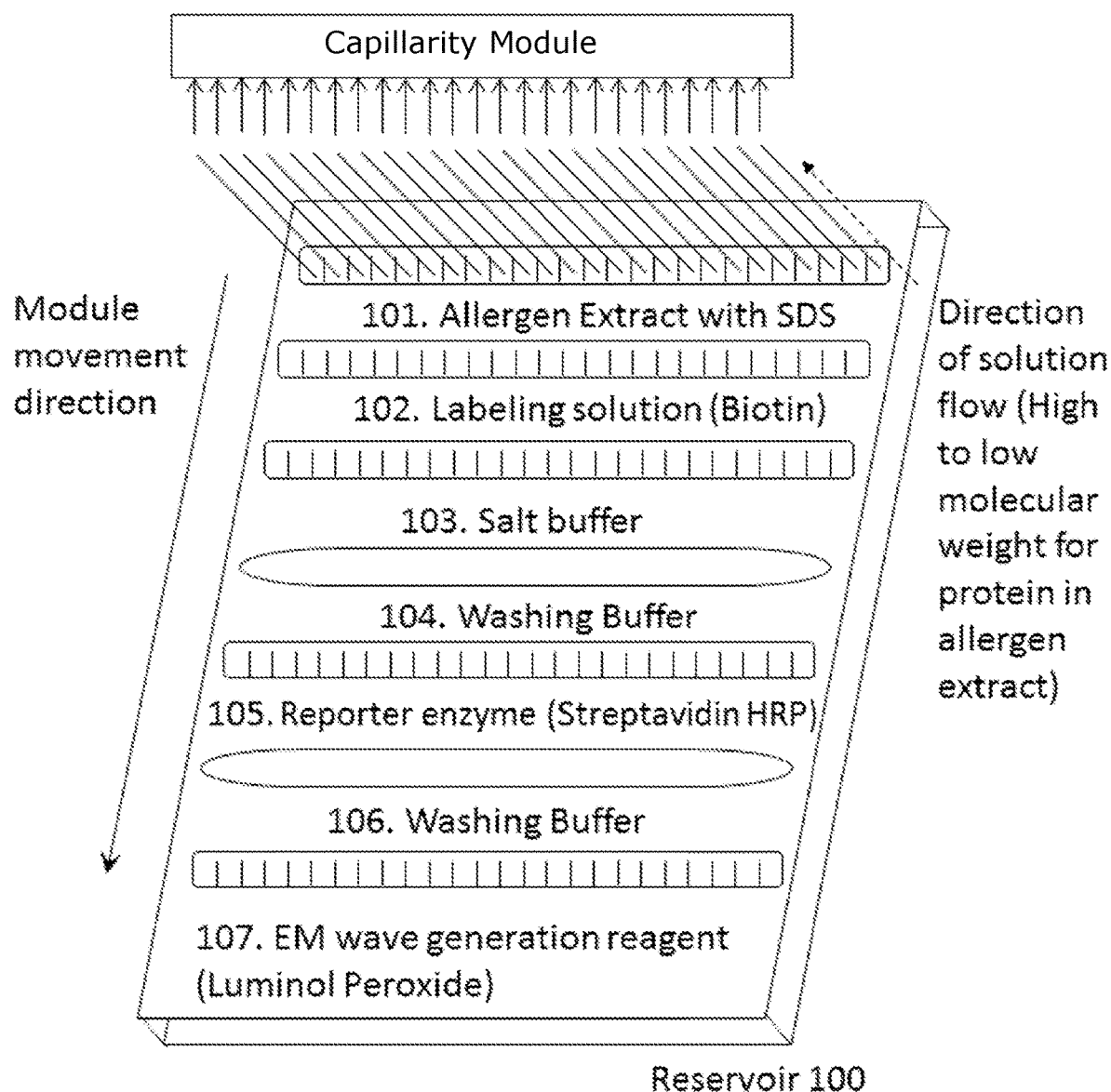
FIG. 3 shows an embodiment of the capillary electrophoresis set-up for a protein content characterization process.

FIG. 3 illustrates a schematic of an embodiment of a protein content characterization system. As seen in the figure, the module of resolving material filled capillaries is moved from the top row to the last row of a reservoir plate. In the embodiment shown, fluids flow from the reservoir, through the capillary and towards the waste collection compartment of the capillary module. In some embodiments, the fluids flow as a result of a vacuum. It is understood that while shown on a single reservoir plate, the fluids need not be located in any, particular reservoir plate and can be obtained from any acceptable receptacle. Protein content protein separation 1a of the protein content characterization process can be performed after allergen extract is supplied to the capillaries from the reservoir of the allergen extract row 101. After protein separation is completed, the module of capillaries is moved to the labeling solution row 102 wherein the binding protein tag 2a is performed by having a protein tag solution supplied to the respective capillaries. In some embodiments, a salt buffer is supplied to the capillaries by the salt buffer row 103 to prevent drying of the capillaries. In some embodiments, after tagging is completed, the module of capillaries is moved to one or more wash buffer rows 104 of the reservoir plate for removing the unbound tags 3a wherein washing buffer is supplied and run through the capillaries to perform one or more washes. The module of the capillaries is then moved to the reporter conjugate solution row 105 wherein a reporter conjugate solution is supplied to the capillaries and allowed to couple to the capillary bound tagged protein for reporter coupling 4a. After coupling is complete, the module of capillaries is moved to the one or more wash buffer rows of the reservoir plate to remove unbound reporter 5a, wherein washing buffer is supplied and run through the capillaries to perform one or more washes. The module of the capillaries is then moved to the electromagnetic wave generation substrate row 107 to undergo protein content signal generation 6a, wherein electromagnetic wave generation substrate is supplied to the capillaries to carry out signal generation. In some embodiments that use HRP as the reporter enzyme, the electromagnetic wave generation substrate comprises Luminol Peroxide in at least sufficient amount to produce electromagnetic waves. In other embodiments that use HRP as the reporter enzyme to catalyze the generation of colored products, 2,2'-Azinobis [3-ethylbenzothiazoline-6-sulfonic acid]-diammonium salt (ARTS), o-phenylenedi amine dihydrochloride (OPD), AmplexRed, 3,3'-diaminobenzidine (DAB), 3-amino-9-ethylcarbazole (AEC), 3,3',5,5'-tetramethylbenzidine (TMB) or Homovanillic acid are used as chromogenic substrates and the intensity of the colored products is measured by an absorbance detector. In some embodiments that use alkaline phosphatase as the reporter enzyme, p-Nitrophenyl Phosphate, Di sodium Salt (PNPP) and 5-Bromo-4-Chloro-3-Indolyl Phosphate/nitroblue tetrazolium (BCIP/NBT) are used as chromogenic substrates. The signal is captured, recorded and/or analyzed. In some embodiments, the signal can be processed by the capillary electrophoresis processor (e.g., ProteinSimple, model WES).

Similar to the schematic of the embodiment shown in FIG. 3, an embodiment of the allergen characterization process is shown in a schematic (shown in FIG. 4) showing a module of resolving material filled capillaries moving from the top row to the last row of a reservoir plate. In the embodiment shown, fluids flow from the reservoir, through the capillary and towards the waste collection compartment of the capillary module. It is understood that while shown on a single reservoir plate, the fluids need not be located in any particular reservoir plate and can be obtained from any acceptable receptacle. In some embodiments, during protein separation 1b, of the component detection process, is performed after allergen extract is supplied to the capillaries from the reservoir in the allergen extract row 201. After protein separation 1b is completed, the module of capillaries is moved to the blocking solution row 202 of the reservoir plate for the blocking 2b, wherein a blocking solution is supplied to the capillaries. After the blocking 2b is completed, the module of capillaries is moved to Ig fluid row 203 for antibody incubation 3b, wherein Ig containing fluids are supplied to the capillaries and coupled with a protein of any size having the corresponding epitopes that the supplied Igs recognize. A wash buffer is supplied to the module of capillaries to remove uncoupled materials 4b. One or more wash buffers can be supplied and run through the capillaries one or more times to perform multiple buffer washes. In tagging bound Ig antibodies 5b, one or more reporter enzymes coupled to an Anti-Ig, the reporter enzyme coupled Anti-Ig solution row 205, is supplied to the capillaries to couple to the capillary bound Ig. During removing unbound Anti-Ig 6b, one or more wash buffers from the one or more wash buffer rows 206 is supplied and run through the capillaries to perform one or more washes. The module of capillaries is then moved to electromagnetic wave generation substrate row 207, wherein an electromagnetic wave generation substrate is supplied to the capillaries to carry out electromagnetic signal generation.

In some embodiments, the wash buffer rows 104 and 106 can be the same one or more rows. In some embodiments, the wash buffer rows 204 and 206 are the same one or more rows, in other embodiments, the wash buffer rows 104, 106, 204, and 206 are the same one or more rows. In some embodiments, the wash buffer rows 104, 106, 204, and 206 are rows filled with one or more wash buffers.

In some embodiments, the process of protein content characterization and allergen characterization can be done together using the same reservoir plate and type of capillary module. Rows 101, 102, 103, 105, 107, 201, 202, 203, 205 and 207 have the same number of wells as the number of capillaries in the capillary module. Reagents supplied in the reservoir plates can be changed according to the process intended for the capillary, either protein content characterization or allergen characterization.

In some embodiments, the allergen extract supplied is extracted from a native source e.g., nuts) using an ionic buffer with detergent or conventional chemical method well known in the art.

In some embodiments after providing the allergen extract in liquid form, the allergen extract is subsequently simultaneously resolved by one or multiple identical capillaries using capillary electrophoresis. In some embodiments, this can be performed with a commercially available platform at an optimized extract concentration located in the allergen extract row 101 of the reservoir plate.

After different proteins from the allergen extract are fixed onto the inside of the capillaries and resolving material is removed, proteins in the desired capillaries can be biotinylated by the labeling solution row 102. In some embodiments, resolved proteins on the capillary are incubated with 10 mM biotinylation reagent for 30 minutes during the binding protein tag 2a to tag allergen extract proteins. In some embodiments the protein is pre-biotinylated, and a salt buffer is present in the labeling solution row 102. The biotinylated proteins on the inside of the capillaries can be subsequently incubated with biotin binding molecules conjugated with light emission catalytic enzyme during the reporter coupling 4a. In some embodiments, the proteins are incubated with Streptavidin conjugated with horseradish peroxidase (HRP), that is provided in reporter enzyme solution row 105, for 30 minutes during the reporter coupling 4a. Uncoupled streptavidin-HRP is then washed away using wash buffer supplied in the wash buffer row 106. In some embodiments where HRP is conjugated to the biotin-binding chemicals, luminol peroxide solution is provided via the electromagnetic wave generation substrate row 107 to the capillaries. The resulting chemiluminescent reaction is catalyzed to emit light during the protein content signal generation 6a. Chemiluminescence or light signal generated in protein content signal generation 6a is recorded at predetermined exposure times along the capillaries. The other capillaries with the same resolved protein therein, are also blocked with non-interfering proteins during blocking 2b of the allergen component detection process. In some embodiments, 5% BSA is present n the blocking solution row 202 and is used during blocking 2b. These capillaries can be subsequently incubated with Ig samples, that is supplied by the Ig fluid row 203, that were found to react or not react with the allergenic material in an independent immunoassay or comparable assay during the antibody incubation 3b. In some embodiments, the incubation occurs over a predetermined time period and at a predetermined temperature (e.g., 2 hours at room temperature). Anti-Ig with light emission catalytic enzyme conjugate from the reporter enzyme coupled Anti-Ig solution row 205 can be supplied to the capillaries to bind to Ig captured on the capillary during the tagging bound antibodies 5b. In some embodiments, anti-Ig with horseradish peroxidase (HRP) conjugate at 10 µg/ml is supplied by the reporter e coupled Anti-Ig solution row 205 and incubated with Ig in the capillaries for 30 minutes. Free anti-Ig are then washed away using wash buffer supplied in the wash buffer row 206. In some embodiments where HRP is conjugated to anti-Ig, luminol peroxide solution is supplied to the capillaries by the electromagnetic wave generation substrate row 207. The resulting chemiluminescent reaction is catalyzed to emit light as described in the protein content characterization signal generation 7b. Signal generated from the electromagnetic wave is recorded in allergic components signal generation 7b at predetermined exposure times along the capillaries. In some embodiments, the platform generates chromatograms with molecular weight scale or isoelectric charge scale on the x-axis and chemiluminescence relative signal on the y-axis in data presentation 8b.

Successively, the area of peaks in the protein content chromatogram with a signal to noise ratio larger than the default threshold are added to obtain the total area under all peaks. Percentage abundance of each peak is calculated using formula (2):

$$\% \text{ Abundance} = \frac{\text{Area of each peak}}{\text{Total area under all peaks}} \times 100\% \quad (2)$$

The concentration of protein corresponding to each molecular weight peak is subsequently calculated using formula (3):

Concentration of protein=% Abundance×allergen extract concentration used (3)

Finally, chromatograms of each of the capillaries incubated with a serum and/or plasma sample panel that reacted with the resolved allergenic protein are inspected for peak appearance. Respective molecular weight, isoelectric charge, and/or molecular functional group of all peaks and the frequency of peak appearance among all samples are recorded. Percentage prevalence corresponding to molecular weight, isoelectric charge and/or molecular functional group can be calculated using formula (4):

$$\% \text{ Prevalence} = \frac{\text{No. of } Ig \text{ samples with positive responses to the protein}}{\text{No. of } Ig \text{ samples in the panel}} \times 100\% \quad (4)$$

Methods and embodiments of methods are further described in relation to an innovative way to detect major and minor components among various groups of individuals. The groups can be defined by different traits, demographic regions, age, ethnicity or combinations thereof. In some embodiments, the samples are selected from two, preferably three or more groups to form a panel.

Chromatograms from each serum and/or plasma sample are inspected for peak appearance. Respective molecular weight, isoelectric charge, and/or molecular functional group of all peaks and the frequency of appearance among all chromatographs are recorded. Percentage prevalence of peaks within each group can be calculated using formula (5).

$$\% \text{ Prevalence} = \frac{\text{No. of } Ig \text{ samples with positive responses to the protein}}{\text{No. of } Ig \text{ samples in the group}} \times 100\% \quad (5)$$

Methods, and embodiments of methods, are also described for designing a reagent intended to effectively detect Ig specific to major and minor components. In some embodiments, all components detected by the panel tested are engineered into a potent allergen product comprised of each component or above the minimum concentration required to detect Ig above a set threshold value. In some embodiments, the threshold value is set according to an assay platform's limit of detection, and in some other embodiments, the threshold value is set as desired. Since most platforms have limited loading capacity, allergen components are also confined by a maximum concentration to avoid occupying capacity better used for other components at or above their minimum concentration. Additionally, and as a result, a sample with Ig specific to any single component at or above the defined threshold concentration for that platform could be assigned a positive result.

The platform and assay dependent minimum concentration of each component can be determined by an embodiment of the method described herein. The testing platform used can be any suitable manual or automated immunoassay process. Whole allergen immunoassay concentration results are obtained from serial dilutions of an Ig sample monosensitized to a single component of the whole allergen. Ig sample dilution factor is identified corresponding to a result equal to a defined lower limit of quantitation, such as 0.1 IU/ml, or in some embodiments to a historical clinically relevant threshold of 0.35 IU/ml, for immunoglobin type E. Successively, whole allergen immunoassay results are obtained from the monosensitized Ig sample pre-diluted to the lower limit of quantitation using serial dilutions of the whole allergen extract. Whole allergen extract dilution factor is identified corresponding to the lower limit of quantitation which is the used to prepare allergen extract with a minimum concentration of the single component.

If monosensitized samples of the component being tested are not available, an isolated fraction of extract obtained using size exclusion chromatography, or anther similar process can be used to identify the specific Ig concentration of the Ig sample. The isolated fraction of the whole allergen extract is then assayed with the diluted Ig sample.

In the examples provided hereinafter, the BioCLIA system (HOB Biotech, Suzhou, China) is used and Ig sample is diluted to arrive at 0.35 IU/ml of sIgE. When a dilution of the allergen extract, or its isolated fraction, reports an IU/ml value equivalent to the defined lower limit of detection, the concentration of the specific component is identified as the minimum component concentration required in an effective assay. Thus, the minimum component concentration is sufficient to detect a threshold amount of sig, within the Ig solution, to meet the predetermined lower limit of quantitation. The goal is to find the lowest amount of component concentration for a sIg to equal or meet the limit of detection. In some embodiments, the threshold amount of Ig is 0.35 IU/ml.

Similar to the minimum concentrations, the maximum concentration of each component of an effective assay can be dependent upon the immunoassay type and platform. The testing platform can be any appropriate manual immunoassay or automated process. The number of components in the allergen extract can first be found during sIg profiling of a patient panel (e.g., allergen characterization, protein content characterization, and biologics content characterization). This Ig sample panel can be selected from two, and sometimes, three or more groups. The groups can be defined by different traits, demographic regions, age, ethnicity or combinations thereof. The minimum concentration of each component can be identified using a method described above. The maximum concentration of each component possible in the platform with which minimum concentrations were defined, is then estimated as when all the other components are at their minimum concentrations. The maximum concentration can be presented mathematically as shown below.

Let n be the number of components found during sig profiling of the sample panel. Let $[Min]_i$ and $[Max]_i$ be the minimum and maximum concentration of component i for an effective assay. Let [R] be the maximum allergen amount that can be loaded onto the platform where the minimum component concentrations were identified. The maximum concentration of component i is then estimated by:

$$[Max]_i = [R] - \sum_{j=1}^{n} [Min]_{j \neq i}$$

A potent allergen product can be formulated for the platform after the minimum and the maximum concentration of the selected components are determined on the platform. The testing platform can be any suitable manual immunoassay or automated process. The number of components in the allergen extract is first determined by sig profiling of an Ig sample panel as described above (e.g., allergen characterization, protein content characterization and biologics content characterization). A potent extract is designed to have each component at a concentration between its minimum and maximum concentration. The content of the potent extract can be presented in a table shown herein in Table 1:

TABLE I

Component content of a potent allergen extract

| Content | Concentration |
| --- | --- |
| Component 1 | Between $[Min]_1$ and $[Max]_1$ |
| Component 2 | Between $[Min]_2$ and $[Max]_2$ |
| . | |
| . | |
| . | |
| Component i | Between $[Min]_i$ and $[Max]_i$ |
| . | |
| . | |
| . | |
| Component n | Between $[Min]_n$ and $[Max]_n$ |

Potent allergen product formulation can comprise supplementing an allergen extract with purified or recombinant components, combining different purified fractions obtained using methods known in the art such as, MWCO filtration or dialysis, or FPLC, or combining any known processes of separation and purification. During the formulation of the potent allergen product, it is understood that components can also be reduced to less than or equal to their maximum concentration.

Although this potent allergen product is defined on an immunoassay platform, the invention is not limited to immunoassay but can also be applied to therapeutic formulation such as those prescribed during immunotherapy and any related applications that require an allergen extract. By using the potent allergen product in immunotherapy, minor components are assured to be present and not just the major components.

In an embodiment of a method of allergy assay, the potent allergen product is to resolve in a capillary electrophoresis system, and subsequently to assay an Ig sample to detect and quantify sig to components in one streamlined protocol. Ig standards of known concentration are to be assayed to generate a calibration curve to quantify sig concentration of Ig samples described previously.

The embodiments disclosed can have one or more of the following advantages:

First, lower prevalence components, the minor components will be reviewed simultaneously with the high prevalence components, the major components, and in the same manner.

Second, differences in the content of source materials can easily be detected by comparing biologics content profile and corresponding Ig sample prevalence data. This comparison can be used to measure lot-to-lot consistency of the source material from the same supplier during allergen product manufacturing to ensure coverage for all components, including major and minor components.

Third, the number and molecular weight of components in the source materials can be found in one assay using only 10 μl of Ig sample. This is compared to 200 μl or more required for the prior art. Moreover, the detection and quantification of major components can be accomplished by using monoclonal antibody specific to the major components as the Ig sample. Previously detected components not responsive to these monoclonal antibodies are reviewed as minor components that have not been extensively studied before.

Fourth, the detection and quantification of different sIgs can be accomplished with 10 μl of Ig sample, while conventional multiplex assays are confined by the availability of purified major allergen components, neglecting minor components.

A comprehensive allergen product having all the desired components of a specific allergen, minor and major components, is present therein. A comprehensive allergen product can be designed for testing on specific platforms. Additionally, a comprehensive allergen product can be designed to be used in immunotherapy such that all of the desired, if not all in total, of the major and minor components and/or biologics are present in sufficient amounts to treat the allergy.

A comprehensive Ig sample can be designed having all the desired sIgs that will react with all desired components of an allergen. A comprehensive allergen reagent can be designed to work with a specific testing platform so that extracts can be standardized to be comprised of all major and minor components.

Example of an Embodiment During Practical Use

Profiling of Pistachio Extract
Extracts Preparation

Pistachio flour was purchased from a commercial provider. Flour was mixed continuously in a sodium bicarbonate-based cell lysis buffer at low temperature for 3h. Debris was pelleted using centrifugation, and the extract was first filtered with a Whatman Grade 4 filter and then with a 0.2 μm filter. Filtered extract was then processed with FPLC and used for the following experiment.

Another batch of ground pistachio was purchased from an allergen material provider. Pistachio powder was mixed continuously in commercial cell lysis buffer at a low temperature overnight. Soluble fraction was obtained after centrifugation and was filtered with a. 0.2 μm filter. Soluble fractions were concentrated using a centrifugal filter with low MWCO membrane and were followed by the experiment thereinafter.

The total protein concentration of the prepared extraction was quantified by BC assay.

II. Protein Content Profiling of Pistachio Extracts

Pistachio extracts were mixed with fluorescent dye and SDS based reduced buffer (Standard Pack 1, ProteinSimple), heated at 95° C. for 5 mins and resolved in multiple resolving material filled capillaries using capillary gel electrophoresis (ProteinSimple, model WES). One of the capillaries was incubated with biotinylation reagent for 30 mins. Excess biotinylation reagent was washed off, and the streptavidin-HRP solution was supplied to the capillary to tag all biotinylated proteins on the capillary. A luminol peroxide mixture was subsequently supplied to the capillary to generate a chemiluminescent signal. The magnitude of the chemiluminescent signal was plotted against increasing molecular weight of the protein for protein content profiling. Chemiluminescent signal was recorded at default exposure times of 2, 4, 8, 16, 32, 64, 128, 256 and 512 seconds. Chromatograms were generated by the capillary electrophoresis platform and plotted in the format of chemiluminescent signal unit versus molecular weight. The baseline and peak assignment of each chromatogram were manually inspected, and the resultant protein content chromatograms are shown in FIGS. 5 and 6. Area of each peak identified was exported to a calculation spreadsheet.

Proteins identified by their molecular weight appeared as chromatogram peaks during protein content profiling of the pistachio extract are listed, along with their percentage abundance, in Table 2 below.

TABLE 2

Protein content profile of pistachio extracts

| Food Supplier | |
| --- | --- |
| MW (kDa) | % Total |
| 5 | 0.06 |
| 7 | 0.19 |
| 7 | 0.26 |
| 8 | 0.26 |
| 10 | 0.25 |
| 11 | 0.12 |
| 12 | 0.13 |
| 14 | 0.22 |
| 15 | 0.26 |
| 16 | 0.22 |
| 18 | 0.40 |
| 19 | 0.17 |
| 21 | 0.13 |
| 22 | 0.12 |
| 23 | 0.16 |
| 24 | 0.18 |
| 25 | 0.76 |
| 26 | 0.11 |
| 27 | 0.67 |
| 28 | 1.23 |
| 29 | 1.06 |
| 30 | 2.62 |
| 31 | 1.22 |
| 32 | 1.38 |
| 35 | 1.12 |
| 36 | 1.95 |
| 38 | 4.49 |
| 39 | 2.20 |
| 41 | 2.79 |
| 43 | 3.53 |
| 44 | 4.71 |
| 48 | 2.37 |
| 49 | 1.74 |
| 50 | 1.89 |
| 53 | 1.88 |
| 54 | 2.18 |
| 57 | 2.52 |
| 58 | 3.25 |
| 60 | 2.41 |
| 61 | 2.50 |
| 63 | 3.25 |
| 65 | 4.26 |
| 69 | 3.97 |
| 74 | 0.79 |
| 77 | 1.54 |
| 80-81 | 0.39 |
| 82 | 2.63 |
| 85 | 0.71 |
| 90 | 2.13 |
| 98 | 2.47 |
| 108 | 3.48 |
| 111 | 2.00 |
| 119 | 1.92 |
| 126 | 1.55 |
| 134 | 2.43 |
| 139 | 0.30 |
| 146 | 1.49 |
| 153 | 1.50 |
| 157 | 2.48 |
| 169 | 1.23 |
| 175 | 1.86 |
| 204 | 3.92 |

| Allergen Supplier | |
| --- | --- |
| MW (kDa) | % Total |
| 3 | 2.71 |
| 4 | 1.32 |
| 6 | 2.33 |
| 7 | 2.07 |
| 8 | 2.07 |

TABLE 2-continued

Protein content profile of pistachio extracts

| | |
|---|---|
| 10 | 1.16 |
| 11 | 0.86 |
| 12 | 0.76 |
| 13 | 0.64 |
| 14 | 0.47 |
| 16 | 1.05 |
| 17 | 1.57 |
| 19 | 1.26 |
| 21 | 0.79 |
| 23 | 1.00 |
| 24 | 1.05 |
| 25 | 1.94 |
| 27 | 1.71 |
| 28 | 0.38 |
| 29 | 4.57 |
| 32 | 4.95 |
| 34 | 1.24 |
| 35 | 1.46 |
| 35 | 1.44 |
| 38 | 8.64 |
| 40 | 2.79 |
| 43 | 4.44 |
| 45 | 2.27 |
| 48 | 1.75 |
| 49 | 2.21 |
| 51 | 1.46 |
| 54 | 1.84 |
| 55 | 1.83 |
| 56 | 2.03 |
| 57 | 2.41 |
| 59 | 1.80 |
| 60 | 2.25 |
| 63 | 1.20 |
| 64 | 2.60 |
| 71 | 1.72 |
| 80 | 2.61 |
| 85 | 2.00 |
| 92 | 1.10 |
| 96 | 1.61 |
| 101 | 1.56 |
| 107 | 1.26 |
| 112 | 1.43 |
| 119 | 0.68 |
| 122 | 1.01 |
| 124-127 | 0.50 |
| 134 | 1.60 |
| 154 | 1.24 |
| 162 | 1.29 |
| 171 | 0.67 |
| 178 | 0.71 |
| 194 | 0.34 |
| 208 | 0.34 |

III. Detection of Components in Pistachio

Serum and plasma samples were tested for sIgE to Pistachio with a 510(*k*) cleared in vitro diagnostic device. All samples with a positive result of 0.35 IU/ml and above were selected to form a panel. The two Pistachio extracts prepared earlier were diluted to 0.1 mg/ml total protein and resolved by molecular weight using capillary gel electrophoresis in multiple capillaries. Capillaries were then blocked with 5% BSA in 0.1M PBS, pH 7.4 and subsequently incubated at room temperature with a positive sIgE sample, with each capillary having 10 μl of a different positive sIgE sample, for 2 hours. Capillaries were then washed and incubated with 0.01 mg/ml of HRP conjugated anti-IgE monoclonal antibody. After washing, a luminol peroxide solution was supplied resulting in a chemiluminescent signal proportional to the concentration of sIgE bound to pistachio protein. Chemiluminescent signal was recorded at default exposure times of 2, 4, 8, 16, 32, 64, 128, 256 and 512 seconds. Chromatograms of each capillary were generated by the capillary electrophoresis platform and plotted in the format of chemiluminescent signal unit versus molecular weight. The baseline and peak assignment of each chromatogram were manually inspected. The resultant immunoassay chromatogram is shown in FIG. 7, The molecular eight of sIgE-bound Pistachio proteins from each positive sIgE sample were tabulated and shown in Table 3 and 4 below.

TABLE 3

Components detected by sample panel at 0.1 mg/ml of allergen extract prepared with Pistachio from a food supplier. "Y" indicates a positive response.

| Ig Sample Number | Molecular Weight (kDa) | | | | | | | | | | | |
|---|---|---|---|---|---|---|---|---|---|---|---|---|
| | 5-9 | 10-13 | 15-19 | 20-21 | 22-24 | 25-26 | 27-29 | 30-34 | 35-37 | 38-41 | 42-46 | 47-49 |
| PP 1 | | Y | | | | | Y | | Y | Y | Y | Y |
| PP 2 | | Y | | | | | Y | | | | | |
| PP 3 - No response | | | | | | | | | | | | |
| PP 4 | | | | | | | | | | Y | Y | |
| PP 5 | | | | | | Y | | Y | Y | Y | Y | |
| PP 6 | | | | | | | | Y | Y | Y | Y | |
| PP 7 - No response | | | | | | | | | | | | |
| PP 8 - No response | | | | | | | | | | | | |
| PP 9 | | | | | | | | Y | Y | Y | Y | |
| PP 10 | | | | | | | Y | Y | | Y | Y | |
| PP 11 | | Y | | | | Y | Y | Y | Y | Y | Y | Y |
| PP 12 - No response | | | | | | | | | | | | |
| PP 13 | | | | | | Y | Y | Y | Y | Y | Y | Y |
| PP 14 | | | | | | | | | | Y | | |
| PP 15 | | | | Y | | | | | | Y | | |
| PP 16 | | | Y | | | | | | | Y | Y | |
| PP 17 | | Y | | | | | | | | | Y | |
| PP 18 | | | | Y | Y | Y | Y | | | | | |
| PP 19 | | | | | | | | | | | | |
| PP 20 | | | | | | Y | | | | Y | Y | |
| PP 21 - No response | | | | | | | | | | | | |
| PP 22 | | | | | | Y | Y | Y | Y | Y | Y | |
| PP 23 - No response | | | | | | | | | | | | |
| PP 24 | | | | | | | | Y | Y | Y | Y | |

TABLE 3-continued

Components detected by sample panel at 0.1 mg/ml of allergen extract prepared with Pistachio from a food supplier. "Y" indicates a positive response.

| Ig Sample | | | | | | | | | | | | |
|---|---|---|---|---|---|---|---|---|---|---|---|---|
| PP 25 | | | | | | | | | | Y | | Y |
| PP 26 | | | Y | | | | | | | | | Y |
| PP 27 | | | | | | Y | Y | Y | | | Y | |
| PP 28 | Y | | | | | | | | Y | Y | Y | |
| PP 29 - No response | | | | | | | | | | | | |
| PP 30 | | | | | | | | | | Y | Y | |
| PP 31 | | | | | | Y | | | | | Y | |
| Total Positive response: (from 24 samples) | 1 | 4 | 1 | 3 | 1 | 7 | 8 | 9 | 9 | 17 | 17 | 6 |
| % Prevalence | 4% | 17% | 4% | 13% | 4% | 29% | 33% | 38% | 38% | 71% | 71% | 25% |

| Ig Sample | Molecular Weight (kDa) | | | | | | | | | | | |
|---|---|---|---|---|---|---|---|---|---|---|---|---|
| Number | 50-56 | 57-59 | 60-62 | 63-79 | 80-81 | 82-109 | 110-123 | 124-127 | 128-150 | 151-172 | 173-193 | 194-204 |
| PP 1 | Y | Y | Y | | | Y | Y | | | | | |
| PP 2 | | | | | | | | | | | | |
| PP 3 - No response | | | | | | | | | | | | |
| PP 4 | Y | Y | Y | | | | | | | | | |
| PP 5 | | | | | | Y | Y | Y | Y | Y | Y | Y |
| PP 6 | | Y | Y | | | | | | | | | |
| PP 7 - No response | | | | | | | | | | | | |
| PP 8 - No response | | | | | | | | | | | | |
| PP 9 | Y | Y | Y | | | Y | Y | Y | Y | Y | Y | Y |
| PP 10 | | | | | | | | | | | | |
| PP 11 | Y | Y | Y | Y | Y | Y | Y | Y | Y | Y | Y | |
| PP 12 - No response | | | | | | | | | | | | |
| PP 13 | Y | Y | Y | Y | Y | Y | Y | Y | Y | Y | Y | Y |
| PP 14 | Y | Y | Y | | | | | | | | | Y |
| PP 15 | Y | Y | Y | Y | | | | | Y | | | |
| PP 16 | | | Y | | | Y | Y | Y | Y | Y | Y | |
| PP 17 | | | | | | | | | | | | |
| PP 18 | Y | Y | | | | | | | | | | |
| PP 19 | | Y | Y | | | Y | | Y | Y | | | |
| PP 20 | Y | Y | Y | | | | | | | | Y | |
| PP 21 - No response | | | | | | | | | | | | |
| PP 22 | Y | Y | Y | | | | | | | | | |
| PP 23 - No response | | | | | | | | | | | | |
| PP 24 | Y | Y | | | | Y | | | | | | |
| PP 25 | | Y | | | | | | | | | | |
| PP 26 | Y | Y | | | | | | | | | | |
| PP 27 | Y | Y | Y | | | | | | | | Y | |
| PP 28 | | Y | Y | | | | | | | Y | | |
| PP 29 - No response | | | | | | | | | | | | |
| PP 30 | Y | | | | | Y | Y | Y | | | | |
| PP 31 | Y | Y | Y | | | | | | | Y | Y | |
| Total Positive response: (from 24 samples) | 15 | 18 | 15 | 3 | 2 | 9 | 7 | 7 | 7 | 7 | 8 | 4 |
| % Prevalence | 63% | 75% | 63% | 13% | 8% | 38% | 29% | 29% | 29% | 29% | 33% | 17% |

TABLE 4

Components detected by sample panel at 0.1 mg/ml of allergen extract prepared with Pistachio from an allergen material supplier. "Y" indicates a positive response.

| Ig Sample | Molecular Weight (kDa) | | | | | | | | | | | |
|---|---|---|---|---|---|---|---|---|---|---|---|---|
| Number | 5-9 | 10-13 | 15-19 | 20-21 | 22-24 | 25-26 | 27-29 | 30-34 | 35-37 | 38-41 | 42-46 | 47-49 |
| PP 1 | Y | Y | | | | | | | Y | Y | Y | Y |
| PP 2 - No response | | | | | | | | | | | | |
| PP 3 | | | | | | | | | | Y | Y | |
| PP 4 | | | | | | | | | | Y | Y | |
| PP 5 | | | Y | Y | | | | Y | Y | Y | Y | Y |
| PP 6 | | | Y | | | | | | Y | Y | | |
| PP 7 | Y | | | | | | | Y | Y | Y | Y | |
| PP 8 | | | | | | | | | | | | |
| PP 9 | | | | | | | | | Y | | Y | |
| PP 10 | | | | | | Y | | | | Y | Y | |

TABLE 4-continued

Components detected by sample panel at 0.1 mg/ml of allergen extract prepared with Pistachio from an allergen material supplier. "Y" indicates a positive response.

| Ig Sample Number | C1 | C2 | C3 | C4 | C5 | C6 | C7 | C8 | C9 | C10 | C11 | C12 |
|---|---|---|---|---|---|---|---|---|---|---|---|---|
| PP 11 | | | | | | | Y | Y | Y | Y | Y | |
| PP 12 | | | | | Y | | | | Y | | | |
| PP 13 | | | | | Y | Y | Y | Y | Y | Y | Y | Y |
| PP 14 | | | | | | | | Y | Y | Y | Y | |
| PP 15 | | | | | | | | | Y | Y | Y | |
| PP 16 - No response | | | | | | | | | | | | |
| PP 17 - No response | | | | | | | | | | | | |
| PP 18 | Y | | | | | | | | | Y | Y | Y |
| PP 19 | | Y | | | | | | | | Y | Y | Y |
| PP 20 | | | | | | | | | Y | Y | Y | |
| PP 21 | | | | | | | Y | | | | | |
| PP 22 | | | | | | | Y | | | Y | Y | |
| PP 23 | Y | | | | | Y | Y | Y | | Y | Y | |
| PP 24 | | Y | | | Y | | | | | Y | Y | |
| PP 25 | | | | | | | | | | Y | Y | Y |
| PP 26 | Y | Y | | | Y | Y | Y | | | | | Y |
| PP 27 - No response | | | | | | | | | | | | |
| PP 28 | Y | | | | Y | | | | Y | Y | Y | |
| PP 29 | | | | | Y | | | Y | | Y | Y | |
| PP 30 | | | | | | | | | | Y | Y | |
| PP 31 | | | | | | | Y | Y | Y | Y | | |
| Total Positive response: (from 27 samples) | 6 | 4 | 2 | 1 | 3 | 4 | 5 | 11 | 13 | 22 | 22 | 7 |
| % Prevalence | 22% | 15% | 7% | 4% | 11% | 15% | 19% | 41% | 48% | 81% | 81% | 26% |

| Ig Sample Number | Molecular Weight (kDa) | | | | | | | | | | | |
|---|---|---|---|---|---|---|---|---|---|---|---|---|
| | 50-56 | 57-59 | 60-62 | 63-79 | 80-81 | 82-109 | 110-123 | 124-127 | 128-150 | 151-172 | 173-193 | 194-204 |
| PP 1 | Y | Y | | | | | | | | | | |
| PP 2 - No response | | | | | | | | | | | | |
| PP 3 | | | | | | | | | | | | |
| PP 4 | Y | Y | | | | Y | | | | | | |
| PP 5 | | Y | | | Y | Y | Y | | Y | Y | Y | |
| PP 6 | | | | | | | | | | | | |
| PP 7 | Y | Y | Y | | Y | Y | Y | | Y | Y | Y | |
| PP 8 | | | | | | | | | | | | |
| PP 9 | | | | | Y | Y | Y | Y | Y | Y | Y | Y |
| PP 10 | | | | | | | Y | | Y | Y | | |
| PP 11 | Y | Y | Y | Y | Y | Y | Y | Y | Y | Y | Y | |
| PP 12 | | | | | | | | | | | | |
| PP 13 | | Y | Y | Y | Y | Y | Y | Y | | | | |
| PP 14 | | | | | | | | | | | | |
| PP 15 | Y | Y | | Y | | | | | | | | |
| PP 16 - No response | | | | | | | | | | | | |
| PP 17 - No response | | | | | | | | | | | | |
| PP 18 | Y | Y | | | | | | | | | | |
| PP 19 | Y | Y | Y | Y | | Y | | | | | | |
| PP 20 | Y | Y | | | | Y | Y | Y | Y | Y | Y | |
| PP 21 | | | | | | | | | | | | |
| PP 22 | Y | Y | Y | Y | | Y | Y | | | Y | | |
| PP 23 | Y | Y | Y | Y | | Y | Y | | | Y | | |
| PP 24 | Y | Y | | | Y | Y | Y | Y | Y | Y | | |
| PP 25 | | Y | | | | | | | | | | |
| PP 26 | Y | Y | | | | Y | | | | | | |
| PP 27 - No response | | | | | | | | | | | | |
| PP 28 | | Y | Y | | | | | | | | | |
| PP 29 | | | | | | Y | Y | | | | | |
| PP 30 | | | | | | | | | | | | |
| PP 31 | | Y | | Y | | Y | Y | Y | Y | | | |
| Total Positive response: (from 27 samples) | 12 | 17 | 7 | 7 | 6 | 14 | 12 | 6 | 8 | 9 | 5 | 1 |
| % Prevalence | 44% | 63% | 26% | 26% | 22% | 52% | 44% | 22% | 30% | 33% | 19% | 4% |

Differences in protein content and percentage prevalence of positive sIgE sample response to proteins resolved by molecular weight of the two source materials were compared as shown in Table 5. Any other protein source material can be characterized in the same manner.

TABLE 5

Pistachio extract protein content profile along with percentage prevalence of positive sIgE sample response

| | MW (kDa) | | | | | | | |
|---|---|---|---|---|---|---|---|---|
| | 5-9 | 10-13 | 15-19 | 20-21 | 22-24 | 25-26 | 27-29 | 30-34 |
| Food Supplier | | | | | | | | |
| % Prevalence | 4% | 17% | 4% | 13% | 4% | 29% | 33% | 38% |
| % Abundance | 0.77 | 0.50 | 0.57 | 0.13 | 0.46 | 0.87 | 2.96 | 5.22 |
| Allergen Supplier | | | | | | | | |
| % Prevalence | 22% | 15% | 7% | 4% | 11% | 15% | 19% | 41% |
| % Abundance | 6.47 | 3.42 | 2.83 | 0.79 | 2.05 | 3.65 | 6.66 | 6.19 |

| | MW (kDa) | | | | | | | |
|---|---|---|---|---|---|---|---|---|
| | 35-37 | 38-41 | 42-46 | 47-49 | 50-56 | 57-59 | 60-62 | 63-79 |
| Food Supplier | | | | | | | | |
| % Prevalence | 38% | 71% | 71% | 25% | 63% | 75% | 63% | 13% |
| % Abundance | 3.07 | 9.48 | 8.24 | 4.11 | 5.95 | 5.77 | 4.91 | 13.81 |
| Allergen Supplier | | | | | | | | |
| % Prevalence | 48% | 81% | 81% | 26% | 44% | 63% | 26% | 26% |
| % Abundance | 2.90 | 11.43 | 6.71 | 3.96 | 7.16 | 4.21 | 2.25 | 5.52 |

| | MW (kDa) | | | | | | | |
|---|---|---|---|---|---|---|---|---|
| | 80-81 | 82-109 | 110-123 | 124-127 | 128-150 | 151-172 | 173-193 | 194-208 |
| Food Supplier | | | | | | | | |
| % Prevalence | 8% | 38% | 29% | 29% | 29% | 29% | 33% | 17% |
| % Abundance | 0.39 | 11.42 | 3.92 | 1.55 | 4.22 | 5.21 | 1.86 | 3.92 |
| Allergen Supplier | | | | | | | | |
| % Prevalence | 22% | 52% | 44% | 22% | 30% | 33% | 19% | 4% |
| % Abundance | 2.61 | 7.53 | 3.12 | 0.50 | 1.60 | 3.20 | 0.71 | 0.68 |

IV. Defining Minimum Concentration of Components

Figure 9:
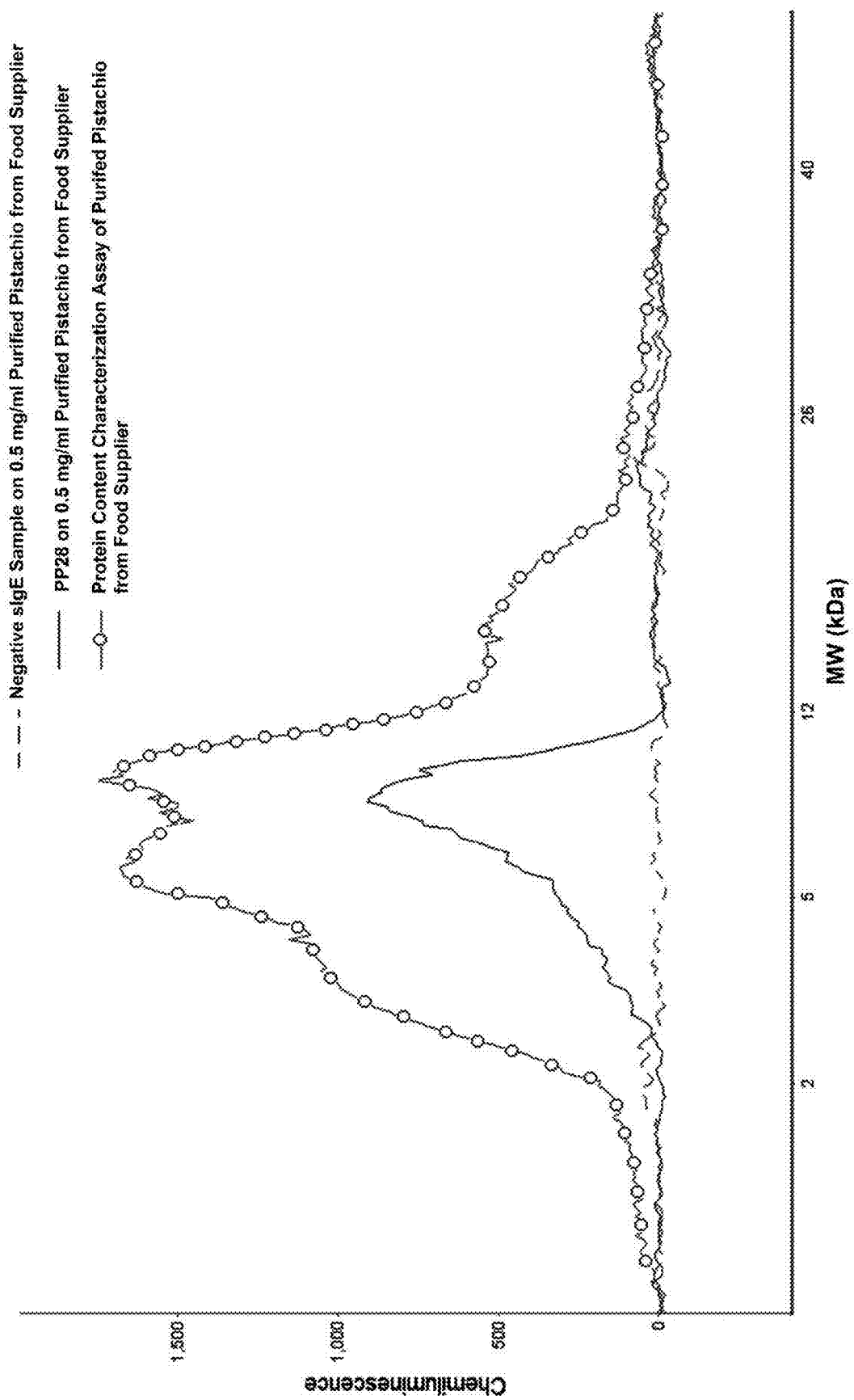
FIG. 9 shows a result of an example capillary electrophoresis protein content characterization assay and its immunoassay chromatogram of an Ig sample sensitized to a purified pistachio fraction.

Sample PP28 listed in Table 3 & 4 responded to proteins sized between 5 and 9 kDa. Using FPLC, proteins in the size range of 5-9 kDa were isolated. The protein content profile of the isolated fraction and its immunoassay result from Sample PP28 and a negative sIgE sample (negative control) is shown in FIG. 9.

Sample PP28 was serially diluted, and each dilution was used to titrate against increasing concentration of biotinylated 5-9 kDa protein until identifying a result plateau on the BioCLIA sIgE Assay platform. At the resultant plateau, a sIgE concentration result of 329 IU/ml was calculated from a dilution of Sample PP28 within the BioCLIA sIgE Assay calibration range (0.35-100 IU/mL). Sample PP28 was then diluted to 0.35 IU/ml, corresponding to sIgE assay positive threshold value, and assayed with serial dilutions of biotinylated 5-9 kDa protein. A minimum concentration of 14 ug/ml of biotinylated 5-9 kDa protein was required for BioCLIA to output a 0.35 IU/ml test result. Thus the minimum concentration, for this specific component weight (5-9 kDa), on this platform (BioCLIA), is 14 µg/nil to obtain the desired 0.35 IU/ml test result if a test sample has an Ig for this component. Once the minimum concentration for all desired components is determined, the maximum concentration of each component, including the component having a weight of 5-9 kDa, can be determined.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

It should also be noted that elements of embodiments may be described in reference to the description of a particular embodiment; however, it is disclosed that elements of disclosed embodiments can be switched with corresponding elements of embodiments with the same name and/or number of other disclosed embodiments.

Depending on the embodiment, certain steps of methods described may be removed, others may be added, and the sequence of steps may be altered. It is also to be understood that the description and the claims drawn to a method may include some indication in reference to certain steps (e.g. numbers, letters, letter and numbers). However, the indication used is only to be viewed for identification purposes and not as a suggestion or requirement as to an order for the steps.

We claim:

1. A method of formulating an allergen product comprising:
   (a) obtaining at least a first allergen source, comprising one or more first allergen components, and a second allergen source comprising one or more second allergen components, wherein at least one of the allergen components in the first or second source is classified as a minor component;
   (b) selecting an immunoassay;
   (c) determining, for the first and second allergen source, a minimum concentration and a maximum concentration for each of the one or more first and second allergen components,
   wherein the determining step comprises determining the minimum concentration by performing the immunoassay with (i) each of the first and second allergen source and (ii) an immunoglobulin (Ig) solution with a known concentration, and determining the minimum concentration as the minimum concentration required to obtain a result representative of the known Ig solution concentration,
   wherein determining the maximum concentration comprises inputting the determined minimum concentration for each of the one or more first and second allergen components into equation:

$$[\text{Max}]_i = [R] - \sum_{j=1}^{n} [\text{Min}]_{j \neq i}$$

where R is maximum allergen component content in the first or second allergen source, n is the number of allergen components in the first or second allergen source, and $[Min]_i$ and $[Max]_i$ are the minimum concentration and the maximum concentration, respectively, (d) formulating an allergen product solution by mixing the at least first and second allergen sources so that the final allergen product solution contains the one or more first and second allergen components present in concentrations at or between the determined minimum and the determined maximum concentrations.

2. The method of claim 1, further comprising: performing the immunoassay with the formulated allergen product and two or more samples, wherein the two or more samples comprise a first Ig sample and a second Ig sample.

3. The method of claim 2, wherein performing the immunoassay with the formulated allergen product comprises separating the first and second one or more allergen components along a first surface and a second surface of an assay device by applying the formulated allergen product to the first surface and second surface, applying the first Ig sample to the first surface and the second Ig sample to the second surface, producing one or more signals indicative of binding at the first and second one or more allergen components, and reporting the signals.

4. The method of claim 2, wherein the immunoassay is quantitative.

5. The method of claim 1, wherein determining the minimum concentration comprises performing the immunoassay with each of the first and second one or more allergen components at two or more titrations of the first and second one or more allergen components, wherein the two or more titrations comprises titrations with decreasing allergen component concentration.

6. The method of claim 1, wherein the one or more first allergen components and the one or more second allergen components are proteins.

7. The method of claim 1, wherein the maximum concentration comprises a maximum concentration that allows for all other of the first and second one or more allergen components to be present at their minimum concentrations required to obtain a result representative of the known Ig solution concentration.

8. The method of claim 2, wherein performing the immunoassay further comprises resolving the first and second one or more allergen components by separating the allergen product comprising the first and second one or more allergen components by size, isoelectric point, molecular functional group or a combination thereof.

* * * * *